United States Patent
Lewis et al.

(10) Patent No.: US 10,114,000 B1
(45) Date of Patent: Oct. 30, 2018

(54) APPARATUS, SYSTEM, AND METHOD FOR MONITORING FLOW IN A PASSAGE

(71) Applicant: mIQroTech, LLC, State College, PA (US)

(72) Inventors: Meade Lewis, State College, PA (US); Justin Stewart, Ponte Vedra Beach, FL (US)

(*) Notice: Subject to any disclaimer, the term of this patent is extended or adjusted under 35 U.S.C. 154(b) by 0 days.

(21) Appl. No.: 15/901,717

(22) Filed: Feb. 21, 2018

(51) Int. Cl.
| | |
|---|---|
| *G01N 33/28* | (2006.01) |
| *G01L 9/04* | (2006.01) |
| *G01N 27/72* | (2006.01) |
| *G01K 13/02* | (2006.01) |
| *G01N 29/02* | (2006.01) |
| *G01N 9/36* | (2006.01) |
| *H04W 84/04* | (2009.01) |

(52) U.S. Cl.
CPC ............ *G01N 33/28* (2013.01); *G01K 13/02* (2013.01); *G01L 9/04* (2013.01); *G01N 9/36* (2013.01); *G01N 27/72* (2013.01); *G01N 29/02* (2013.01); *G01K 2013/026* (2013.01); *G01N 2291/02818* (2013.01); *H04W 84/042* (2013.01)

(58) Field of Classification Search
None
See application file for complete search history.

(56) References Cited

U.S. PATENT DOCUMENTS

| | | | | |
|---|---|---|---|---|
| 7,442,291 B1* | 10/2008 | Discenzo | ............ | B01D 35/143 210/443 |
| 7,657,392 B2* | 2/2010 | Gysling | ................ | G01N 9/002 702/128 |
| 2003/0146749 A1* | 8/2003 | Srinivasan | ........... | G01N 17/006 324/263 |
| 2016/0061640 A1* | 3/2016 | Joshi | ........................ | G01F 1/00 73/197 |
| 2018/0058202 A1* | 3/2018 | Disko | ................... | E21B 49/087 |

* cited by examiner

*Primary Examiner* — Harshad R Patel
(74) *Attorney, Agent, or Firm* — James M. Smedley LLC; James Michael Smedley, Esq.

(57) ABSTRACT

An assembly for sensing flow material in a passage of a member is disclosed. The assembly has a housing, a communication device disposed at least partially in the housing, and a controller disposed at least partially in the housing. The assembly also has a sensor array disposed at least partially in the housing, and an external-surface-mounting attachment portion configured to non-intrusively attach the assembly to a surface. The sensor array includes a pressure sensor, a density sensor, a corrosion sensor, and a vibration sensor. The controller controls the communication device to transmit sensed data collected by the sensor array at a frequency of between about one transmission per second and about fifty transmissions per second.

29 Claims, 5 Drawing Sheets

APPARATUS, SYSTEM, AND METHOD FOR MONITORING FLOW IN A PASSAGE

TECHNICAL FIELD

The present disclosure generally relates to an apparatus, system, and method for monitoring flow in a passage, and more particularly to an apparatus, system, and method for monitoring flow of material through a passage of a member.

BACKGROUND

Fluid-carrying structures such as oil pipelines transport fluid (e.g., refined oil or crude oil) over any desired distance (e.g., relatively short distances within industrial facilities and/or relatively long distances of hundreds of miles). Pipelines are typically constructed from structural materials such as steel that may be subject to corrosion and material failure. For example, structural damage and failures are estimated to cost the pipeline industry tens of billions of U.S. dollars each year. Additionally, leaks and spills caused by structural damage and failure of pipelines cause spills that significantly damage the environment.

Varying conventional approaches are used to monitor fluid-carrying structures such as pipelines to attempt to detect potential failures before they occur and cause environmental and financial damage. For example, some monitoring technologies are inserted through pipeline walls. Although monitoring data may be obtained using these technologies, the penetration involved with inserting the monitoring technology may itself cause leaks to pipelines. Other approaches utilize radioactive materials (e.g., Uranium, Cesium, Americium, and/or Plutonium) in monitoring pipelines, which are harmful to personnel and the environment. Accordingly, conventional techniques do not provide a safe technique for effectively monitoring flow in passages such as pipelines that avoid damage to the structures being monitored and the surrounding environment.

The exemplary disclosed apparatus, system, and method are directed to overcoming one or more of the shortcomings set forth above and/or other deficiencies in existing technology.

SUMMARY OF THE DISCLOSURE

In one exemplary aspect, the present disclosure is directed to an assembly for sensing flow material in a passage of a member. The assembly includes a housing, a communication device disposed at least partially in the housing, and a controller disposed at least partially in the housing. The assembly also includes a sensor array disposed at least partially in the housing, and an external-surface-mounting attachment portion configured to non-intrusively attach the assembly to a surface. The sensor array includes a pressure sensor, a density sensor, a corrosion sensor, and a vibration sensor. The controller controls the communication device to transmit sensed data collected by the sensor array at a frequency of between about one transmission per second and about fifty transmissions per second.

In another aspect, the present disclosure is directed to a method. The method includes providing a non-invasive sensor array at a surface of a member transporting flow material, using the non-invasive sensor array to sense a pressure of the flow material, a density of the flow material, and a temperature of the flow material, and wirelessly transmitting data of the sensed pressure, the sensed density, and the sensed temperature to a flow monitoring module including computer-executable code stored in non-volatile memory. The method also includes using artificial intelligence to perform predictive analysis based on the sensed pressure, the sensed density, and the sensed temperature, and wirelessly transmitting result data of the predictive analysis to a user interface

DETAILED DESCRIPTION AND INDUSTRIAL APPLICABILITY

Figure 1:
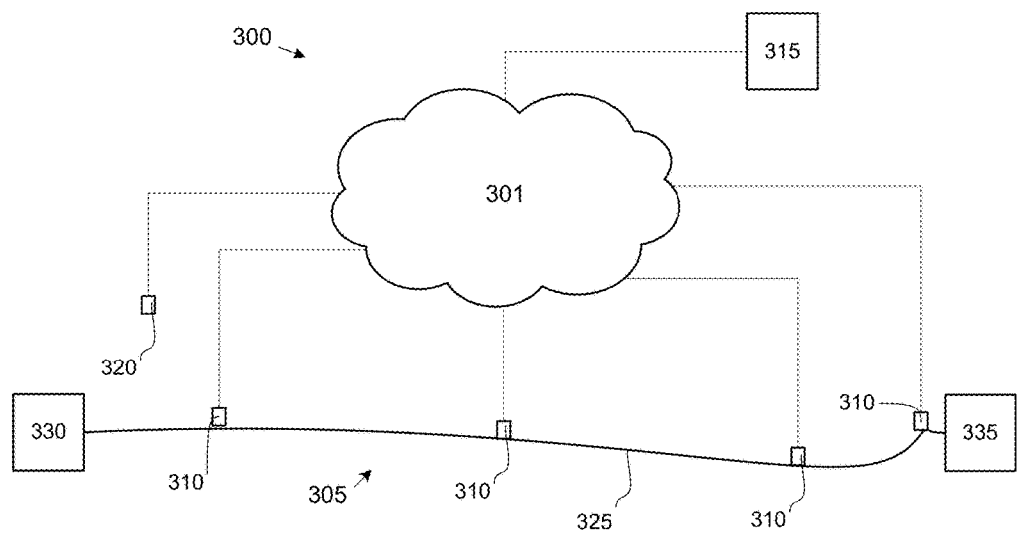
FIG. 1 is a schematic view of an exemplary embodiment of the present invention.

FIG. 1 illustrates an exemplary system 300 for monitoring a passage system 305. For example, system 300 may be any suitable system for monitoring flow in a passage. For example, system 300 may be used in any application for monitoring flow of material through a passage of a member (e.g., an elongated member). For example, system 300 may be any suitable system for monitoring a flow carried in a passage of a structural member. For example, system 300 may be any suitable system for pipeline monitoring (e.g., when passage system 305 is a pipeline such as, e.g., an oil pipeline, a natural gas pipeline, any pipeline transporting fossil fuels, a water pipeline, a waste or wastewater pipeline, a pipeline transporting oxygen, carbon dioxide, air, chemicals, and/or any other fluid material such as gaseous fluid or liquid fluid material). For example, system 300 may include a sensor assembly that may be a pipeline monitoring assembly (e.g., a refined oil pipeline monitoring assembly or a crude oil pipeline monitoring assembly) configured to be externally attached to a pipeline. Also for example, system 300 may be any suitable system for monitoring a flow of material through a material-transporting passage of a machine, e.g., when passage system 305 may be part of a vehicle (e.g., a motor vehicle, aircraft, and/or ship) and/or industrial or commercial equipment, and/or a structure (e.g., buildings of any size and/or structures such as bridges). For example, system 300 may be any suitable system for detecting unsuitable operation (e.g., leaking) of a material-transporting passage such as, e.g., a passage transporting a flow of fluid material. For example, system 300 may be any suitable system for monitoring a flow of any suitable material through a passage.

Figure 2:
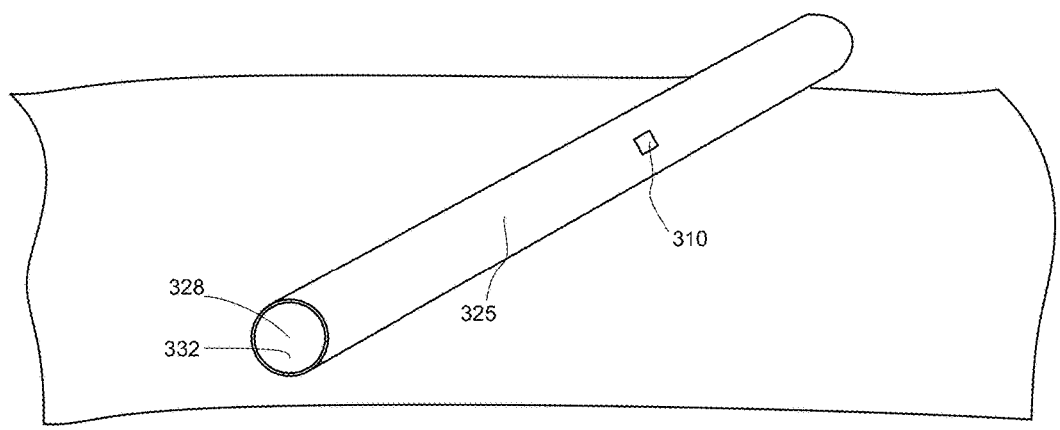
FIG. 2 is a schematic view of an exemplary embodiment of the present invention.

Passage system 305 may be any system that transports an exemplary flow material 332 such as, for example, gaseous fluid material, liquid fluid material, and/or solid material (e.g., solid material capable of acting in a fluid-like manner). As illustrated in FIGS. 1 and 2, passage system 305 may include a plurality of members 325. For example, members 325 may be any suitable structural member for transporting exemplary flow material 332, e.g., a structural member including a passage 328. For example, member 325 may be a structural piping member having passage 328 (e.g., any suitable substantially hollow passage or channel). For example, member 325 may be a structural metal (e.g., steel) pipe, a structural plastic (e.g., PVC) pipe, and/or a structural member formed from any suitable material for forming a passage for transporting flow material. Member 325 may have any suitable shape for transporting flow material such as, for example, a circular or elliptical shape, a square or rectangular shape, a polygonal shape, and/or any other suitable shape. Also for example, member 325 may be any suitable member for transporting a flow of material through exemplary vehicles, equipment, and/or structures disclosed, e.g., above. For example, member 325 may also be a relatively thin metal tubing (e.g., copper tubing) such as a passage for transporting fluid through a vehicle (e.g., fuel, hydraulic fluid, and/or coolant), industrial equipment, and/or a structure.

Exemplary flow material 332 may be any suitable material that may be transported via members 325. For example, flow material 332 may be a fluid material (e.g., gaseous fluid material and/or liquid fluid material), a solid material capable of acting in a fluid-like manner (e.g., a granular material such as fine aggregate such as sand and/or coarse aggregate such as stones that may be mixed with water or other fluid), and/or a combination of any suitable gaseous fluid, liquid fluid, and/or fluid-like solid material. For example, flow material 332 may be a fossil fuel in fluid form (e.g., refined oil or crude oil, natural gas, and/or any other suitable type of fossil fuel), water, air, oxygen, carbon dioxide, any suitable chemical in fluid form, waste or wastewater, and/or any other suitable material that may flow through a passage.

Flow material 332 may be, for example, transported under pressure through members 325 of passage system 305. For example, a plurality of members 325 may be attached together and placed above and/or underground to transfer flow material 332 over any suitable distance (e.g., members 325 may be attached together by fasteners, welding, and/or any other suitable technique to form passage system 305). For example, passage system 305 may transport flow material 332 (e.g., under pressure) between a plurality of locations. For example as illustrated in FIG. 1, passage system 305 may transport flow material 332 between a first location 330 and a second location 335. For example, locations 330 and 335 may be one or more of an industrial activity (e.g., refinery, chemical production facility, drilling platform or location, and/or any other suitable industrial facility), commercial activity utilizing flow material 332 (e.g., a factory or other production facility, an airport, a city, a port, and or any other suitable commercial activity), multiple locations in a vehicle utilizing flow material 332, and/or multiple locations in the same structure or in different structures. For example, locations 330 and 335 may be located at any suitable distance from each other such as, e.g., tens or hundreds of feet (e.g., different points or locations in the same vehicle, structure, and or facility), thousands of feet (e.g., points or locations in differing vehicles, structures, and/or facilities), and/or several miles, dozens of miles, hundreds of miles, and/or thousands of miles from each other (e.g., pipelines transporting flow material 332 over relatively long distances).

As illustrated in FIG. 1, system 300 may include may include a sensor assembly 310, a flow monitoring module 315, and a user interface 320. For example, system 300 may include a plurality of sensor assemblies 310. Sensor assembly 310, flow monitoring module 315, and user interface 320 may be connected for example via network 301, which may be similar to exemplary network 201 disclosed below regarding FIG. 7.

Figure 3:
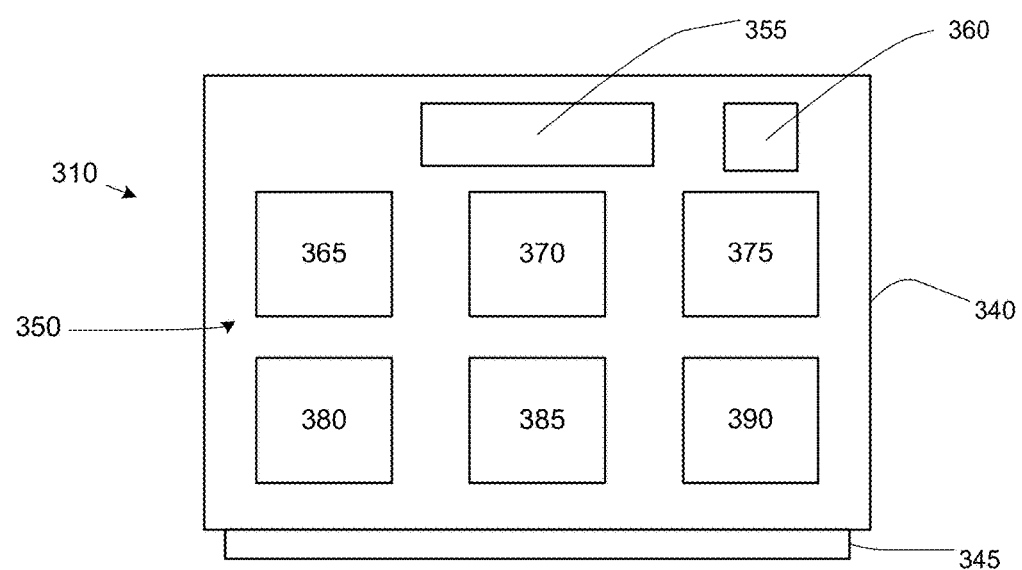
FIG. 3 is a schematic view of an exemplary embodiment of the present invention.
Figure 4:
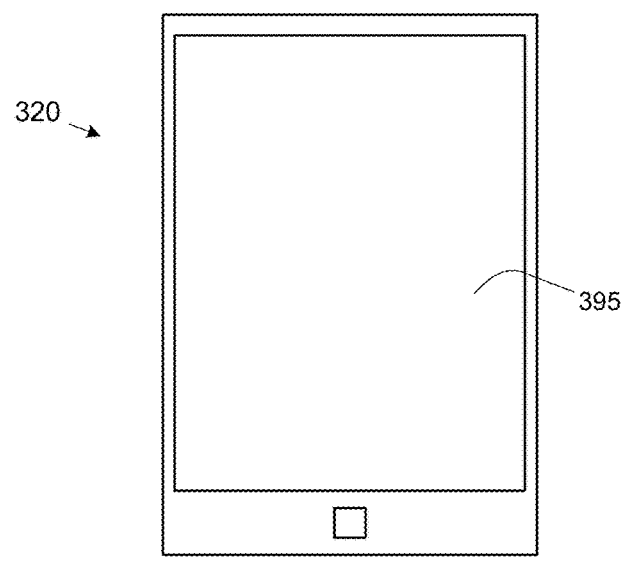
FIG. 4 is a schematic view of an exemplary embodiment of the present invention.

Sensor assembly 310 may be any suitable sensor assembly for monitoring properties of a flow material. As illustrated in FIG. 3, sensor assembly 310 may include a housing 340, an attachment portion 345, a sensor array 350, and a communication device 355. Sensor array 350 and communication device 355 may be housed at least partially or substantially entirely within housing 340. Attachment portion 345 may attach sensor assembly 310 to passage system 305.

Housing 340 may be any suitable structural assembly for containing and/or attachment of components of sensor assembly 310. For example, housing 340 may be a structural assembly having any suitable shape (e.g., rectangular prism, cylindrical, cubic, and/or any other suitable shape) and including one or more cavities for containing components of sensor assembly 310. Housing 340 may also be any suitable housing for protecting components of sensor assembly 310 from the elements (e.g., precipitation, wind, exposure to heat and light, and/or any other environmental or manmade effects), sealing interior cavities of housing 340 against the intrusion of debris and/or other undesirable material, and/or protection from intrusion or tampering from unauthorized users, animals, and/or vegetation. Housing 340 (e.g., as well as other components of sensor assembly 310) may be formed from any suitable materials for containing, protecting, and/or sealing components of sensor assembly 310 such as, for example, polymer material, structural metal (e.g., structural steel), co-polymer material, thermoplastic and thermosetting polymers, resin-containing material, polyethylene, polystyrene, polypropylene, epoxy resins, phenolic resins, Acrylanitrile Butadiene Styrene (ABS), Polycarbonate (PC), Mix of ABS and PC, Acetal (POM), Acetate, Acrylic (PMMA), Liquid Crystal Polymer (LCP), Mylar, Polyamid-Nylon, Polyamid-Nylon 6, Polyamid-Nylon 11, Polybutylene Terephthalate (PBT), Polycarbonate (PC), Polyetherimide (PEI), Polyethylene (PE), Low Density PE (LDPE), High Density PE (HDPE), Ultra High Molecular Weight PE (UHMW PE), Polyethylene Terephthalate (PET), PolPolypropylene (PP), Polyphthalamide (PPA), Polyphenylenesulfide (PPS), Polystyrene (PS), High Impact Polystyrene (HIPS), Polysulfone (PSU), Polyurethane (PU), Polyvinyl Chloride (PVC), Chlorinated Polyvinyl chloride (CPVC), Polyvinylidenefluoride (PVDF), Styrene Acrylonitrile (SAN), Teflon TFE, Thermoplastic Elastomer (TPE), Thermoplastic Polyurethane (TPU), and/or Engineered Thermoplastic Polyurethane (ETPU), or any suitable combination thereof.

Attachment portion 345 may be any suitable member, assembly, or device for attaching sensor assembly 310 (e.g., housing 340) to a portion of passage system 305 so that a flow of exemplary flow material 332 through passage system 305 may be measured. For example, attachment portion 345 may attach sensor assembly 310 (e.g., housing 340) to an external surface of passage system 305 such as, e.g., an external surface of member 325. For example as illustrated in FIG. 2, attachment portion 345 may attach sensor assembly 310 (e.g., housing 340) to an external surface of a wall portion of member 325, wherein the internal surface of the wall portion of member 325 may form passage 328 through which flow material 332 may be transported. Accordingly for example, attachment portion 345 may attach sensor assembly 310 (e.g., housing 340) to member 325 so that sensor assembly 310 is separated from flow material 332

(e.g., flowing through passage 328) by a wall portion of member 325 (e.g., a relatively thin structural wall of member 325 such as, for example, a structural steel section, a plastic section, and/or a structural section of any suitable type of material for forming member 325). Accordingly for example, attachment portion 345 may attach sensor assembly 310 at a location that is relatively close to a flow of flow material 332. For example, attachment portion 345 may be an external-surface-mounting attachment portion configured to non-intrusively attach sensor assembly 310 to a surface of passage system 305 (e.g., attach sensor assembly 310 to member 325 without penetrating, piercing, and/or puncturing a wall portion of member 325). For example, attachment portion 345 may allow sensor array 350 to serve as a noninvasive sensor array disposed at a surface of member 325 transporting flow material 332.

Attachment portion 345 may attach sensor assembly 310 (e.g., housing 340) to passage system 305 by any suitable technique. For example, attachment portion 345 may include a non-penetrating attachment device that may attach sensor assembly 310 to passage system 305 without penetrating any portion of passage system 305 (e.g., a wall portion of member 325). For example, attachment portion 345 may include a threaded attachment device, a bolted attachment device, a snap-fit attachment device, a friction-fit attachment device, an adhesive attachment device, a hook and loop attachment device, a magnetic attachment device, and/or any other suitable mechanical attachment device. For example, attachment portion 345 may be integrally formed with or attached to housing 340 and may extend about a perimeter of member 325 to attach sensor assembly 310 to member 325. For example, attachment portion 345 may include a clamping device to allow sensor assembly 310 to be a clamp-on sensor assembly (e.g., attachment portion 345 clamps around member 325). Also for example, attachment portion 345 may include magnetic, adhesive, and/or mechanical fastening components that attach housing 340 directly to a surface of member 325. Also for example, attachment portion 345 may include portions that extend to the ground (e.g., a tripod and/or other free-standing structural elements) that support housing 340 to be in a position adjacent to an exterior surface of member 325. Further for example, attachment portion 345 may include elastic members (e.g., compression and/or tension members) that urge housing 340 to remain in a position adjacent to and/or bearing against an exterior surface of member 325. Further for example, attachment portion 345 may not tap into passage system 305 (e.g., penetrate, pierce, and/or puncture a portion or section of member 325). For example, attachment portion 345 may attach housing 340 to member 325 (e.g., or other portion of passage system 305) without damaging and/or deforming any portions of passage system 305. For example, housing 340 may be integrally formed with and/or attached to attachment portion 345, and attachment portion 345 may also be attached to an exterior surface of passage system 305 (e.g., an exterior surface of member 325) without penetrating, piercing, and/or puncturing exterior surface portions of passage system 305. For example, attachment portion 345 may attach sensor assembly 310 substantially completely externally to passage system 305 (e.g., to member 325).

Communication device 355 may be any suitable device for communicating data between sensor assembly 310 and any other component of system 300. For example, communication device 355 may include any suitable transceiver device (e.g., transmitter device and/or receiver device) for transmitting data sensed by sensors of sensor array 350 to other components of system 300 (e.g., to flow monitoring module 315 via network 301) and also for receiving data from other components of system 300. For example, communication device 355 may receive and transmit data as disclosed below regarding exemplary communication techniques of FIG. 7. For example, communication device 355 may wirelessly transmit data by any suitable technique such as, e.g., wirelessly transmitting data via 4G LTE networks (e.g., or any other suitable data transmission technique for example via network 301). For example, communication device 355 may transmit data collected by sensor array 350 of sensor assembly 310 substantially continuously. For example, communication device 355 may transmit data collected by sensor assembly 310 (e.g., to other components of system 300) several times per second and/or many times per second (e.g., up to 20 times per second and/or up to 50 times per second or more). For example, communication device 355 may wirelessly transmit data collected by sensor assembly 310 (e.g., to other components of system 300) between about 40 and 45 times per second, for example, up to about 42 times per second. For example, sensor array 350 may control communication device 355 to transmit sensed data collected by sensor array 350 at a frequency of between about one transmission per second and about fifty transmissions per second. Also for example, sensor array 350 may control communication device 355 to transmit (e.g., wirelessly transmit) sensed data collected by sensor array 350 at a frequency of between about ten transmissions per second and about fifty transmissions per second.

Sensor array 350 may for example include a controller 360 for controlling an operation of sensors of sensor array 350 and communication device 355. Controller 360 may include for example a micro-processing logic control device or board components. Also for example, controller 360 may include input/output arrangements that allow it to be connected (e.g., via wireless and/or electrical connection) to sensors of sensor array 350, communication device 355, flow monitoring module 315, and/or user interface 320 (e.g., via network 301 and/or via direct communication). For example, controller 360 may control an operation of sensor assembly 310 based on input received from flow monitoring module 315 and/or user interface 320 via communication device 355 and may control a transmission of output from sensors of sensor array 350 via communication device 355. For example, controller 360 may communicate with components of system 300 via wireless communication and/or via electrical lines (e.g., electrical line communication to sensors of sensor array 350 and/or communication device 355). For example, controller 360 may control sensors of sensor array 350 and/or communication device 355 so that sensor assembly 310 acts as an Internet of Things (IoT) device that may provide data to and/or be controlled by system 300 as a data-providing device.

Sensors of sensor array 350 may collect data associated with a flow of flow material 332 through passage 328. Sensor array 350 may include any suitable sensors for measuring any suitable properties associated with flow material 332, a flow of flow material 332, and/or properties of portions of passage system 305. For example, sensor array 350 may include a vibration sensor 365, a location sensor 370, a pressure sensor 375, a density sensor 380, a corrosion sensor 385, a temperature sensor 390, and/or any other suitable type of sensor for measuring properties of flow material 332 and/or portions of passage system 305. Also for example, sensor array 350 may include a sonic boom detection sensor. For example, sensor array 350 may include any suitable sensor for detecting a sonic boom (e.g., a sonic boom caused by jets, rifles, and/or lightning) that may for example cause valves of passage system 305 to malfunction or operate unsuitably.

Vibration sensor 365 may be any suitable sensor for measuring vibrations of portions of passage system 305. For example, vibration sensor 365 may be any suitable sensor for measuring vibrations of member 325 such as, e.g., vibrations of a wall portion of member 325 forming passage 328 carrying a flow of flow material 332. For example, vibration sensor 365 may be any suitable member vibration sensor for measuring a frequency of vibration of a structural member. For example, vibration sensor 365 may be any suitable device for measuring a frequency range of vibration and/or a transverse sensitivity. For example, vibration sensor 365 may be a displacement sensor, a velocity sensor, and/or an accelerometer. For example, vibration sensor 365 may be a cantilever-type vibration sensor, a piezo-electric vibration sensor, and/or any other suitable type of sensor for measuring vibration. For example, vibration sensor 365 may include components such as a servo, piezoelectric, potentiometric, and/or strain gauge accelerometer. Also for example, vibration sensor 365 may include components such as an electromagnetic transducer, a tachometer generator, a capacitance proximity sensor, and/or an eddy current sensor probe. For example, vibration sensor 365 may be any suitable sensor that may measure vibrations associated with deteriorated and/or damaged portions of passage system 305 (e.g., deteriorated and/or damaged wall portions of member 325). For example, vibration sensor 365 may be any suitable sensor that may detect abnormal vibrations of a given portion of passage system 305 based that given portion being damaged, worn, deformed, deteriorated, and/or having leaks.

Location sensor 370 may be any suitable sensor for measuring a geographic location such as, for example, a geo-positioning sensor. For example, location sensor 370 may be a global positioning system sensor or any other suitable type of sensor for sensing location with suitable accuracy (e.g., for pinpointing a location of sensor assembly 310 along passage system 305). For example, location sensor 370 may provide a precise location of sensor assembly 310 of within about 10 feet, within about 5 feet, within about 3 feet (e.g., within about 3½ feet, for example, within 3.6 feet), and/or within about 1 foot.

Pressure sensor 375 may be any suitable non-invasive sensor (e.g., non-intrusive sensor) for measuring a pressure of flow material 332 flowing through passage 328 without being disposed in passage 328 and/or penetrating through a wall portion of member 325. For example, pressure sensor 375 may be a flow material pressure sensor that includes a strain gauge that is disposed on an exterior surface of member 325. For example, the exemplary strain gauge of pressure sensor 375 may measure a strain of a wall portion of member 325, from which a pressure within member 325 may be determined (e.g., based on using known and/or determined properties of member 325 and a measured member strain to determine pressure of flow material 332). Also for example, pressure sensor 375 may be an ultrasound pressure sensor, a fiber-optic sensor, an acoustic pressure sensor, a multi-frequency pressure monitoring sensor, and/or any other suitable type of pressure sensor that may measure a pressure of flow material 332 flowing through passage 328 while mounted on an exterior surface of member 325. It is also contemplated that pressure sensor 375 may utilize components such as resonance-detecting components, thermal-conductivity-detecting components, and/or ionization-detecting components. For example, pressure sensor 375 may be any suitable type of non-invasive pressure sensor for providing pressure output for measuring pressure differences of flow material 332 within passage system 305.

Density sensor 380 may be any suitable sensor for measuring a density of flow material 332 flowing through passage 328 without being disposed in passage 328 and/or penetrating through a wall portion of member 325. For example, density sensor 380 may be any suitable non-invasive (e.g., non-intrusive sensor) fluid density sensor for measuring an internal density of flow material 332 flowing in passage 328 of member 325. For example, density sensor 380 may be any suitable sensor for locating air pockets, measuring cavitation, and/or identifying debris within passage 328 (e.g., regardless of a nominal diameter or width of member 325 and/or passage 328). For example, density sensor 380 may be a non-radioactive density sensor (e.g., a sensor that does not utilize radioactive materials in detecting density). Also for example, sensor array 350 may be a non-radioactive sensor array (e.g., a sensor array that does not utilize radioactive materials in sensing). For example, density sensor 380 may be an ultrasonic sensor. For example, density sensor 380 may be a flow material density sensor that includes an ultrasonic transducer and a device for emitting ultrasonic pulses that may be measured by the transducer and/or additional components. For example, density sensor 380 may measure density of flow material 332 by measuring an acoustic impedance of flow material 332. For example, density sensor 380 may emit an ultrasonic wave that may pass through flow material 332, reflect off of a rear wall portion of member 325, and return to density sensor 380 (e.g., a density of flow material 332 may be determined based on a measured speed of the wave and/or time it takes the wave to pass through flow material 332). Also for example, properties of member 325 may be known or determined, which may be used to adjust output of density sensor 380 to determine the density of flow material 332. Further for example, density sensor 380 may include components for measuring structural vibration resonance frequency of portions of passage system 305, which may be used to detect density and/or viscosity of flow material 332.

Corrosion sensor 385 may be any suitable sensor (e.g., non-intrusive sensor) for measuring corrosion of portions of passage system 305 and/or a presence of fragments (e.g., corroded or deteriorated fragments of an interior portion of member 325) in flow material 332. For example, corrosion sensor 385 may be any suitable sensor (e.g., non-intrusive sensor) for measuring internal corrosion of member 325 (e.g., corrosion of interior wall portions of member 325 forming passage 328). For example, corrosion sensor 385 may be any suitable sensor for sensing magnetic interference within flow material 332. For example, corrosion sensor 385 may be any suitable sensor for detecting debris within flow material 332 (e.g., by detecting magnetic interference), which may increase in a downstream direction of passage system 305 (e.g., may increase moving in a direction of flow of flow material 332). For example, corrosion sensor 385 may be a flow material corrosion sensor that includes a magnetometer (e.g., or any other suitable device that detects a magnetic interference in a flow of material). For example, corrosion sensor 385 may be any suitable type of non-invasive sensor for detecting wash such as metallic wash (e.g., metallic components that may be present in flow material 332). Also for example, corrosion sensor 385 may be an ultrasonic sensor, sensor for detecting changes in magnetic properties (e.g., a sensor for performing eddy testing), an electrical-resistance-testing sensor (e.g., any suitable sensor for detecting electrical resistance), a sensor utilizing peltier-based measurement, and/or any other suitable sensor for determining corrosion of member 325.

Temperature sensor 390 may be any suitable sensor for measuring a temperature of flow material 332 flowing in passage 328 and/or measuring a temperature of portions of passage system 305. For example, temperature sensor 390 may either directly or indirectly measure an expansion and/or contraction of flow material 332 and/or member 325. For example, temperature sensor 390 may determine a temperature based on heat conductivity determination. For example, properties of member 325 may be known or determined (e.g., sectional thickness, amount by which a member may be heated, and/or any other suitable properties). Using these known or determined properties of member 325, a thermal value of member 325 that is sensed by temperature sensor 390 may be adjusted based on heat conductivity attributes of member 325 that may be derived from known or determined values of member 325. A temperature of flow material 332 based on sensing a temperature of member 325 may thereby be obtained. Also for example, temperature sensor 390 may be a resistance temperature detector sensor, a thermal-pulse-emitting sensor, a thermal-ribbon sensor, an on-pipe thermal sensor, and/or any other suitable non-intrusive sensor for measuring a temperature of flow material 332 and/or member 325.

Although the exemplary illustration of FIG. 3 illustrates six different sensors 365, 370, 375, 380, 385, and 390, sensor array 350 may include any number of sensors that may measure multiple properties. For example, a single sensor may measure any number of properties and may therefore serve as one or more of sensors 365, 370, 375, 380, 385, and/or 390 (e.g., one or more of sensors 365, 370, 375, 380, 385, and/or 390 may be the same sensor). For example, a single ultrasonic sensor may be density sensor 380 and corrosion sensor 385. Accordingly for example, sensor array 350 may include one, a few, or many sensors that may sense some or all of a vibration, a location, a pressure, a density, corrosion, temperature, and/or any other desired properties of flow material 332 and/or portions of passage system 305. Also for example, sensor array 350 may include, e.g., a sonic boom detection sensor (e.g., as disclosed for example above).

For example, any desired number of sensor assemblies 310 may be disposed on passage system 305. Depending for example on a length, size, and/or importance of some or all segments of passage system 305, one, several, many, dozens, hundreds, and/or thousands or more of sensor assemblies 310 may be attached to passage system 305 to measure properties of flow material 332 at any desired locations. For example, sensor assemblies 310 may be disposed at any desired substantially constant and/or variable intervals along a length of passage system 305.

Returning to FIG. 1, flow monitoring module 315 may communicate with other components of system 300 via network 301 (e.g., as disclosed below regarding FIG. 7). Flow monitoring module 315 may also be partially or substantially entirely integrated with one or more components of system 300 such as, for example, network 301, user interface 320, and/or one or more sensor assemblies 310. Flow monitoring module 315 may include components similar to the exemplary components disclosed below regarding FIGS. 6 and 7. For example, flow monitoring module 315 may include computer-executable code stored in non-volatile memory. Flow monitoring module 315 may also include a processor, or alternatively, a processor for processing data associated with system 300 may be partially or substantially entirely integrated into any portion (e.g., or combination of portions) of system 300 (e.g., network 301, flow monitoring module 315, user interface 320, and/or one or more sensor assemblies 310).

Flow monitoring module 315 may be configured to retrieve, store, process, and/or analyze data transmitted from one or more sensor assemblies 310 to flow monitoring module 315. For example, flow monitoring module 315 may operate using data from any desired number or sensor assemblies 310 such as, for example, one, two, several, dozens, hundreds, and/or thousands or more sensor assemblies 310 (including, e.g., vibration data, location data, pressure data, density data, corrosion data, temperature data, and/or any other suitable data describing any other desired properties of flow material 332 and/or portions of passage system 305).

Flow monitoring module 315 may perform analysis using the data received from sensor assemblies 310 to for example predict potential failure, leaks, and/or other unsuitable operation of passage system 305 before such unsuitable operation may occur. For example, flow monitoring module 315 may utilize sophisticated machine learning and/or artificial intelligence techniques to perform predictive analysis using some or substantially all data collected by sensor assemblies 310. For example, system 300 (e.g., flow monitoring module 315) may for example utilize the collected data to prepare and submit (e.g., via network 301, for example via wireless transmission such as via 4G LTE networks) datasets and variables to cloud computing clusters and/or other analytical tools (e.g., predictive analytical tools) which may analyze such data using artificial intelligence neural networks. Flow monitoring module 315 may for example include cloud computing clusters performing predictive analysis. For example, flow monitoring module 315 may utilize neural network-based artificial intelligence to predictively assess risk (e.g., potential failure of portions of passage system 305 based on continuously collected data transmitted from sensor assemblies 310). For example, system 300 (e.g., flow monitoring module 315) may use the collected data to predict a longevity of operation of some or all portions of passage system 305. For example, the exemplary neural network may include a plurality of input nodes that may be interconnected and/or networked with a plurality of additional and/or other processing nodes to determine a predicted result. For example, exemplary neural networks of system 300 may determine a predicted result of a given portion of passage system 305 to be one of the following exemplary predicted results: "no problem" or "all clear" (e.g., no failure or unsuitable operation predicted during a predetermined time period), a soft alert such as a warning (e.g., no imminent danger of failure, but indications of possible future unsuitable operation exist), and/or an urgent warning (e.g., imminent failure or unsuitable operation is predicted).

For example, exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. For example, exemplary artificial intelligence processes may also include processing for training a machine learning model to predict a longevity of passage system 305 (e.g., including potential failures of passage system 305) based on data collected by sensor assemblies 310. For example, the prediction algorithms and approach may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets. Also for example, exemplary artificial intelligence processes may include processing for training a machine learning model to predict a longevity of passage system 305 (e.g., including potential failures of passage system 305) based on data collected by sensor assemblies 310.

For example, exemplary artificial intelligence processes of system 300 may include using data (e.g., such as density data of flow material 332 measured by density sensor 380) collected by one or more sensor assemblies 310 to identify air pockets, cavitation, a presence of debris, and/or a flow direction within passage 328. Also for example, exemplary artificial intelligence processes of system 300 may include using data (e.g., such as corrosion data measured by corrosion sensor 385) collected by one or more sensor assemblies 310 to identify a rate at which members 325 may be corroding. Further for example, exemplary artificial intelligence processes of system 300 may include using data (e.g., such as pressure data measured by pressure sensor 375) collected by one or more sensor assemblies 310 to measure pressure differences between different sensor assemblies 310 to predict potential locations of unsuitable operation of passage system 305. Additionally for example, exemplary artificial intelligence processes of system 300 may include using data (e.g., such as vibration data measured by vibration sensor 365) collected by one or more sensor assemblies 310 to identify potential leaks and/or deteriorating portions of passage system 305 that may fail. Also for example, exemplary artificial intelligence processes of system 300 may include using data (e.g., such as location data measured by location sensor 370) collected by one or more sensor assemblies 310 to pinpoint and prioritize competing locations of potential future unsuitable operation (e.g., identify and prioritize locations of passage system 305 to be remediated to avoid future failure). Further for example, exemplary artificial intelligence processes of system 300 may include using data (e.g., such as temperature data measured by temperature sensor 390) collected by one or more sensor assemblies 310 to predict potential areas of failure by identifying portions of passage system 305 having abnormal temperatures and/or experiencing unsuitable expansion and/or contraction. For example, system 300 may provide predicted results for some or all monitored portions of passage system 305 such as the exemplary results disclosed above (e.g., "no problem" or "all clear," soft alerts such as a warning, and/or urgent warnings). For example, if a given sensor assembly 310 provides data indicating a large increase in vibration of a given member 325 (e.g., as sensed by vibration sensor 365) occurring contemporaneously or nearly contemporaneously with a sharp decrease of sensed pressure at that location (e.g., based on sensed data provided by pressure sensor 375 and location sensor 370), system 300 may issue an urgent warning indicating currently-occurring and/or imminent member failure and leakage (e.g., oil spill). System 300 may make predictions and issue warnings based on any suitable combination of sensed data and/or changes in sensed data that may indicate any given number of potential scenarios. For example, a large increase in temperature of flow material 332 at a given location as sensed by temperature sensor 390 and location sensor 370 may indicate a likelihood of undesired combustion and an urgent warning may be issued. Also for example, less significant swings or changes in collected date may result in system 300 issuing a warning (e.g., "soft alert"). System 300 may operate (e.g., using artificial intelligence) to issue any suitable number of possible predictive results based on any suitable combination of collected data and/or changes in collected data.

For example, system 300 (e.g., flow monitoring module 315) may utilize continuously collected data from sensor assemblies 310, which may include thousands, millions, and/or billions of data points, to perform predictive analysis using artificial intelligence and/or machine learning. System 300 (e.g., flow monitoring module 315) may for example use the continuously-growing body of data collected by sensor assemblies 310 to establish benchmarks and metrics for defining a suitable range of operation of passage system 305 (e.g., that can be used in conjunction with other similar exemplary passage systems to benchmark suitable operation, and/or which may be used as a comparison against data indicating an unsuitable operation). For example, system 300 (e.g., flow monitoring module 315) may use substantially all available data to continuously refine predictive analysis for identifying potential failure and/or unsuitable operation of passage system 305.

User interface 320 may be any suitable user interface for receiving input and/or providing output (e.g., raw data and/or results of predictive analysis described above) to a user. For example, user interface may be, for example, a touchscreen device (e.g., of a smartphone, a tablet, a smartboard, and/or any suitable computer device), a computer keyboard and monitor (e.g., desktop or laptop), an audio-based device for entering input and/or receiving output via sound, a tactile-based device for entering input and receiving output based on touch or feel, a dedicated user interface designed to work specifically with other components of system 300, and/or any other suitable user interface (e.g., including components and/or configured to work with components described below regarding FIGS. 1 and 2). For example, user interface 320 may include a touchscreen device of a smartphone or handheld tablet. For example, user interface 320 may include a display 395 (e.g., a computing device display, a touchscreen display, and/or any other suitable type of display) that may provide raw data and/or predictive analysis results to a user. For example, display 395 may include a graphical user interface to facilitate entry of input by a user and/or receiving output. For example, a user may utilize user interface 320 to query raw data results and/or enter parameters to define a set of desired output (e.g., portions of passage system 305 that are most likely to fail within a specified time period such as, for example, the next 30 days, the next 6 months, the next year, the next several years, and/or the next decade or longer time period). Also for example, system 300 may provide alerts to a user via output transmitted to user interface 320 (e.g., alerts pushed to a user via user interface 320) for example if a portion of passage system 305 is predicted to imminently fail and/or if significant, sudden changes occur regarding collected data (e.g., one or more sensor assemblies 310 report a large increase or decrease in values that may indicate a significant probability of failure such as, for example, a sharp drop in measured pressure by pressure sensor 375). System 300 may also send such alerts by alternative methods such as, for example, via text message, email, and/or recording sent by telephone.

The exemplary disclosed apparatus, system, and method may be used in any suitable application for monitoring flow in a passage. For example, the exemplary disclosed apparatus, system, and method may be used in any application for monitoring flow of material through a passage of a member.

For example, the exemplary disclosed apparatus, system, and method may be used in monitoring a flow carried in a passage of a structural member such as, e.g., in pipeline monitoring (e.g., an oil pipeline or a chemical pipeline), monitoring of flow through a material-transporting passage of a machine such as a vehicle (e.g., a motor vehicle, aircraft, and/or ship) and/or industrial or commercial equipment, and/or monitoring of flow through a structure (e.g., buildings of any size and/or structures such as bridges). For example, the exemplary disclosed apparatus, system, and method may be used in any suitable application for detecting unsuitable operation (e.g., leaking) of a material-transporting passage such as, e.g., a passage carrying a flow of fluid.

Figure 5:
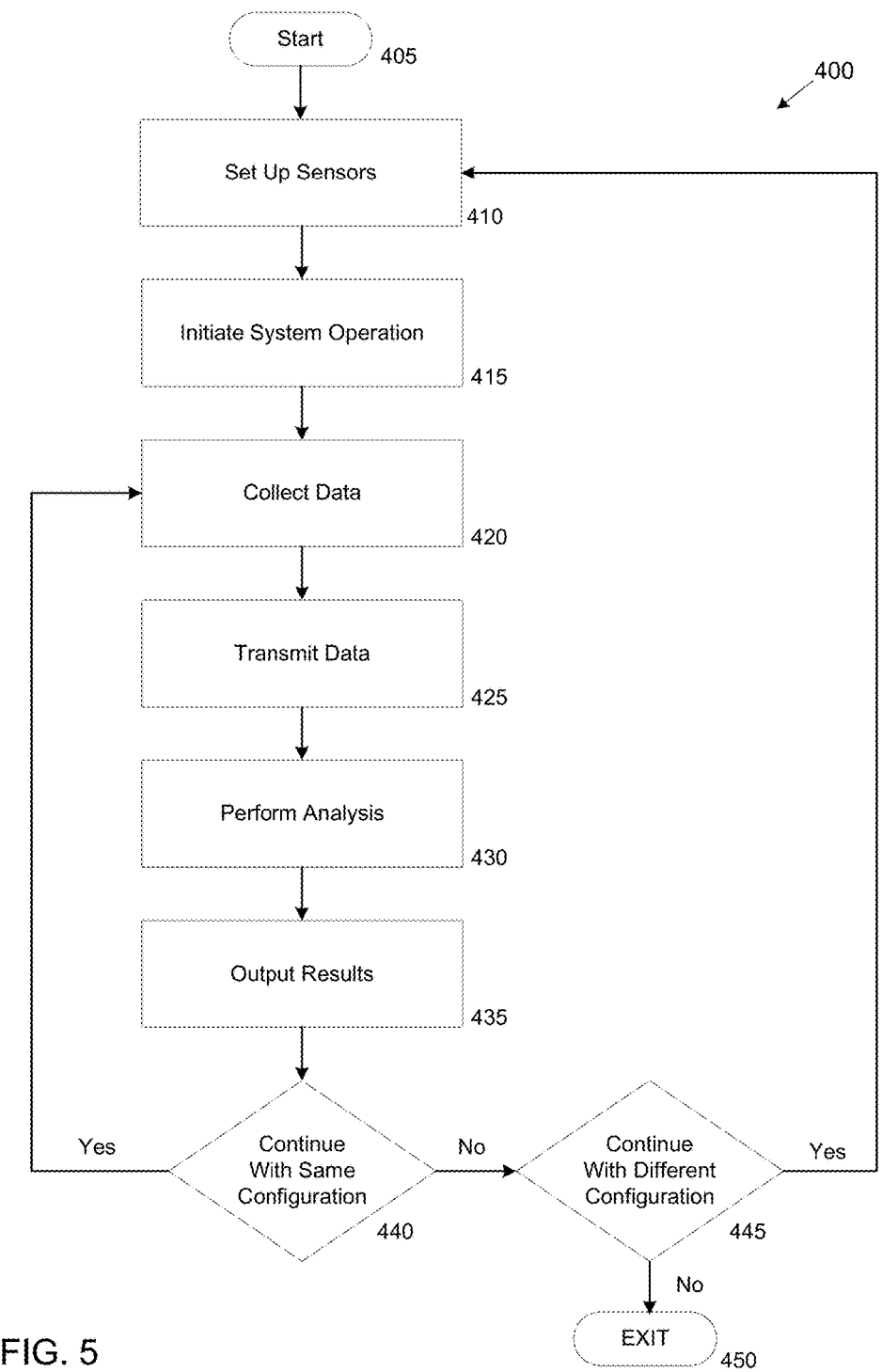
FIG. 5 illustrates an exemplary process for manufacturing the exemplary apparatus.

An exemplary operation of the exemplary disclosed apparatus, system, and method will now be described. For example, FIG. 5 illustrates an exemplary process 400. Process 400 starts at step 405. At step 410, users may place sensor assemblies 310 in any desired configuration. Users may place sensor assemblies 310 at portions of passage system 305 as disclosed for example above. As disclosed for example above, any number of sensor assemblies 310 may be placed to monitor passage system 305 at any desired locations and in any desired configuration.

At step 415, an operation of system 300 may be initiated. System 300 may for example be initiated based on user input provided via user interface 320 and/or automatically by system 300 (e.g., by flow monitoring module 315) based on predetermined parameters, a predetermined time period, and/or analysis performed by system 300 based on processes similar to the exemplary processes disclosed for example above.

At step 420, sensor assemblies 310 may collect data as disclosed for example above. At step 425, data collected by sensor assemblies 310 (e.g., by sensors 365, 370, 375, 380, 385, and/or 390) may be transmitted from sensor assemblies 310 as disclosed for example above (e.g., via communication device 355) to flow monitoring module 315. It is also contemplated that collected data of select sensor assemblies 310 may also be directly transmitted to user interface 320 (e.g., upon parameters and/or queries inputted by a user via user interface 320).

At step 430, system 300 (e.g., flow monitoring module 315) may perform predictive analysis and other analysis and processes using the collected data as disclosed, for example, above. At step 435, results of the analysis performed at step 430 and/or raw collected data may be provided to a user by transmission (e.g., wireless transmission and/or any other suitable transmission as disclosed for example herein) to user interface 320. Alerts based on the collected data and predictive analysis performed at step 430 may also be transmitted to a user via user interface 320. Also for example, system 300 may send results and alerts via text message, email, webpage, and/or recording sent by telephone. At step 435, a user may also use user interface 320 to query and sort results of predictive analysis by, for example, location of passage system 305, time period (e.g., upcoming month or year), and/or type of existing and/or potential failure or unsuitable operation. Also for example, a user may enter additional parameters and/or input to modify the configuration or display of results on user interface 320.

At step 440, system 300 may continue to collect data using a same configuration of sensor assemblies 310 for any amount of time desired by a user and/or as determined automatically by system 300. For example, system 300 may repeat steps 420, 425, 430, and 435 for any desired period of time. If a user and/or system 300 (e.g., based on analysis and/or predetermined criteria) determine that data should no longer be collected using a same configuration of sensor assemblies 310, process 400 may proceed to step 445.

At step 445, a user and/or system 300 (e.g., based on analysis and/or predetermined criteria) may determine that data should be collected using a different configuration of sensor assemblies 310. Process 400 may return to step 410, and a user may physically rearrange sensor assemblies 310 relative to passage system 305 as desired and/or based on prompts from system 300 (e.g., based on predefined criteria and/or based on options generated using analysis performed by system 300 to further optimize monitoring of passage system 305). System 300 may then repeat steps 415, 420, 425, 430, 435, 440, and/or 445 as disclosed above based on any desired monitoring plan. When a user and/or system 300 determine that data collection should be stopped (e.g., for maintenance of system 300 and/or to end monitoring of passage system 305), then process 400 ends at step 450.

The exemplary disclosed apparatus, system, and method may provide an effective technique for safely monitoring a flow of material through a passage of a structural member without damaging the structural member and without causing harm to personnel or the environment. For example, the exemplary disclosed apparatus, system, and method may provide a technique for measuring a plurality of properties of a flow through a passage at a fast rate (e.g., providing sensor output many times per second via efficient transmission such as wireless transmission). Also for example, the exemplary disclosed apparatus, system, and method may provide a technique for monitoring flow in a structural member without penetrating or tapping the structural member and without the use of potentially harmful materials such as radioactive materials. Further for example, the exemplary disclosed apparatus, system, and method may analyze the sensed data to perform predictive analysis to identify potential future structural damage and failure that may be proactively remediated to avoid environmental damage and/or financial loss.

Figure 6:
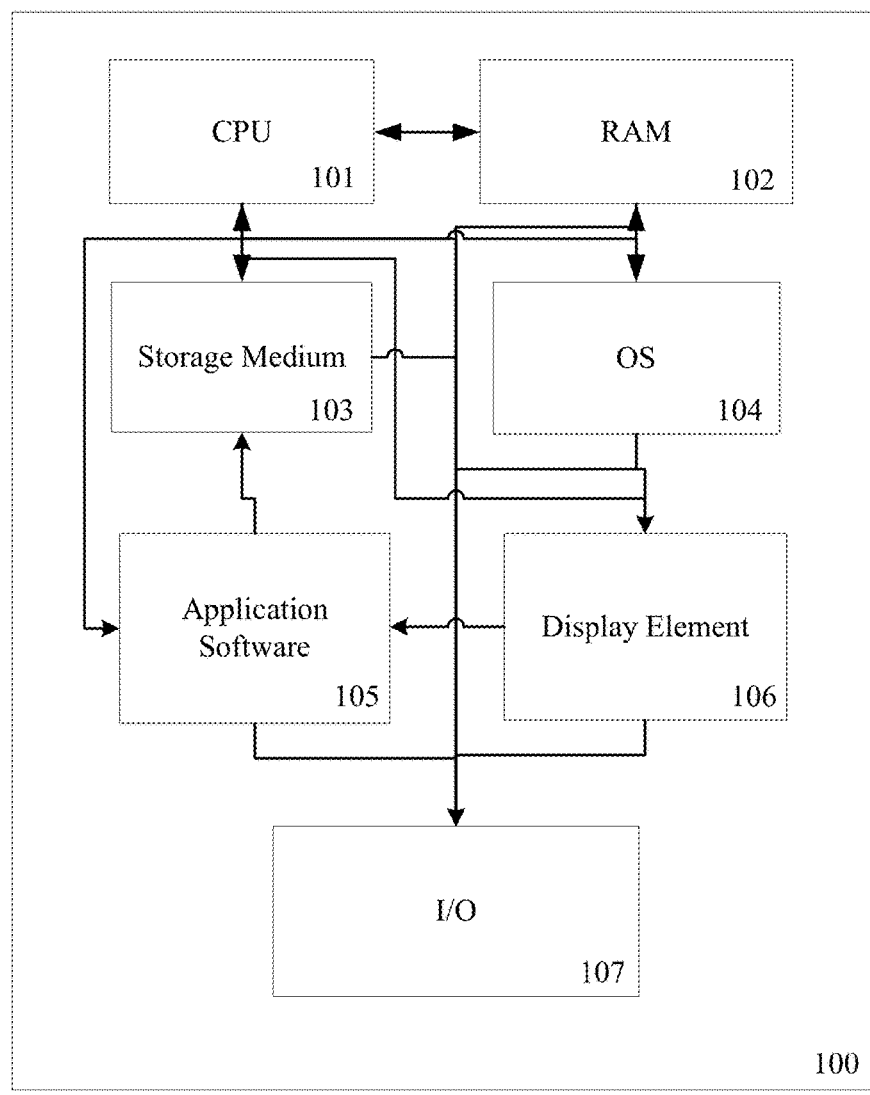
FIG. 6 is a schematic illustration of an exemplary computing device, in accordance with at least some exemplary embodiments of the present disclosure.

An illustrative representation of a computing device appropriate for use with embodiments of the system of the present disclosure is shown in FIG. 6. The computing device 100 can generally be comprised of a Central Processing Unit (CPU, 101), optional further processing units including a graphics processing unit (GPU), a Random Access Memory (RAM, 102), a mother board 103, or alternatively/additionally a storage medium (e.g., hard disk drive, solid state drive, flash memory, cloud storage), an operating system (OS, 104), one or more application software 105, a display element 106, and one or more input/output devices/means 107, including one or more communication interfaces (e.g., RS232, Ethernet, Wifi, Bluetooth, USB). Useful examples include, but are not limited to, personal computers, smart phones, laptops, mobile computing devices, tablet PCs, touch boards, and servers. Multiple computing devices can be operably linked to form a computer network in a manner as to distribute and share one or more resources, such as clustered computing devices and server banks/farms.

Various examples of such general-purpose multi-unit computer networks suitable for embodiments of the disclosure, their typical configuration and many standardized communication links are well known to one skilled in the art, as explained in more detail and illustrated by FIG. 7, which is discussed herein-below.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Figure 7:
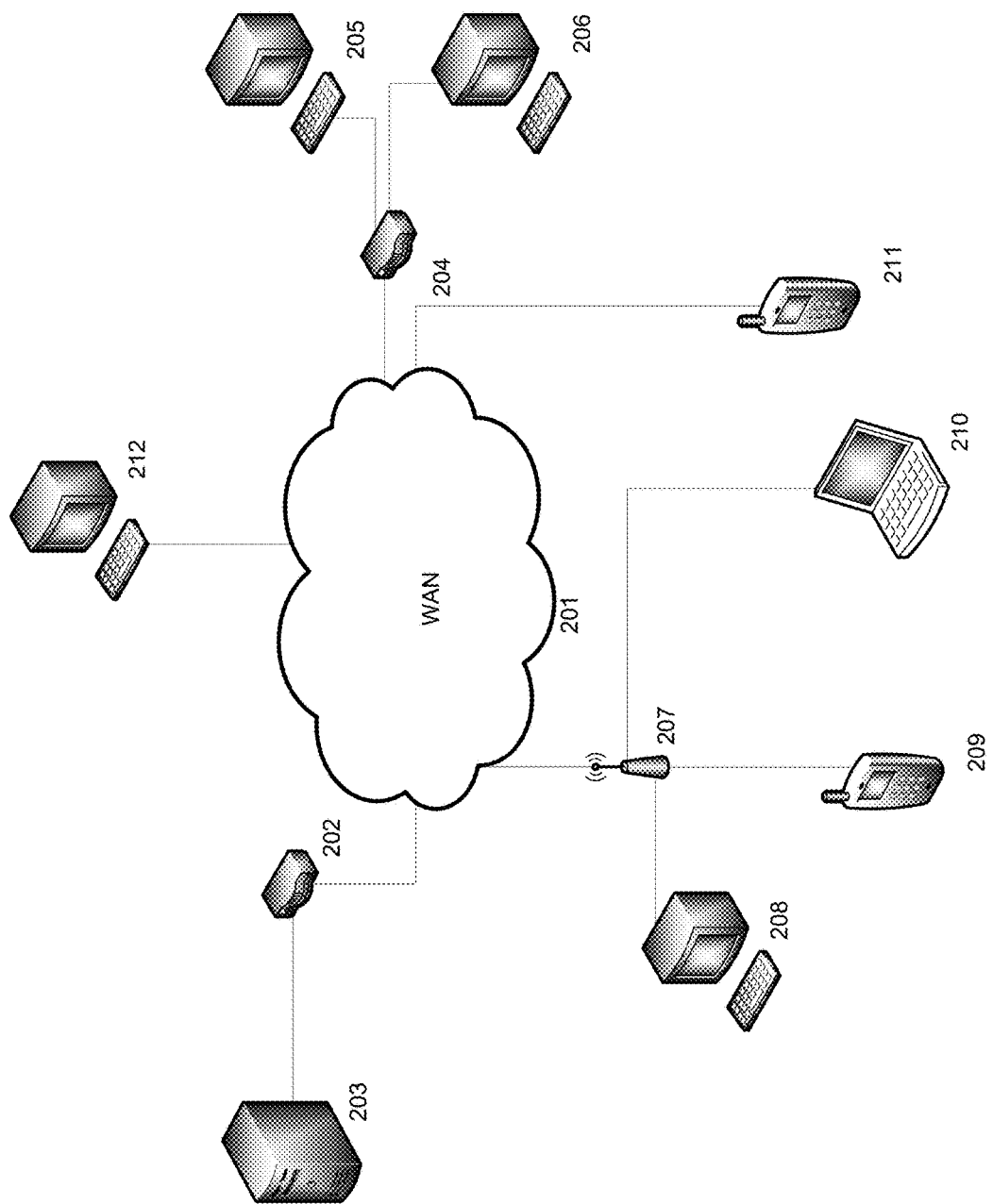
FIG. 7 is a schematic illustration of an exemplary network, in accordance with at least some exemplary embodiments of the present disclosure.

Referring to FIG. 7, a schematic overview of a system in accordance with an embodiment of the present disclosure is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 7, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present disclosure may or may not utilize one or more routers 202. One of ordinary skill in the art would appreciate that there are numerous ways server 203 may connect to WAN 201 for the exchange of information, and embodiments of the present disclosure are contemplated for use with any method for connecting to networks for the purpose of exchanging information. Further, while this application refers to high speed connections, embodiments of the present disclosure may be utilized with connections of any speed.

Components or modules of the system may connect to server 203 via WAN 201 or other network in numerous ways. For instance, a component or module may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GMS, 3G, 4G) to the WAN 201. One of ordinary skill in the art will appreciate that there are numerous ways that a component or module may connect to server 203 via WAN 201 or other network, and embodiments of the present disclosure are contemplated for use with any method for connecting to server 203 via WAN 201 or other network. Furthermore, server 203 could be comprised of a personal computing device, such as a smartphone, acting as a host for other computing devices to connect to.

The communications means of the system may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation C, C++, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed apparatus, system, and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. An assembly for sensing flow material in a passage of a member, comprising:
   a housing;
   a communication device disposed at least partially in the housing;
   a controller disposed at least partially in the housing;
   a sensor array disposed at least partially in the housing; and
   an external-surface-mounting attachment portion configured to non-intrusively attach the assembly to a surface;
   wherein the sensor array includes a pressure sensor, a density sensor, a corrosion sensor, and a vibration sensor;
   wherein the controller controls the communication device to transmit sensed data collected by the sensor array at a frequency of between about one transmission per second and about fifty transmissions per second; and
   wherein the sensed data includes at least one of a density data sensed by the density sensor and a corrosion data sensed by the corrosion sensor.

2. The assembly of claim 1, wherein the sensor array further includes a temperature sensor and a location sensor.

3. The assembly of claim 1, wherein the pressure sensor is a flow material pressure sensor that includes a strain gauge.

4. The assembly of claim 1, wherein the density sensor is a flow material density sensor that includes an ultrasonic transducer.

5. The assembly of claim 1, wherein the corrosion sensor is a flow material corrosion sensor that includes a magnetometer.

6. The assembly of claim 1, wherein the vibration sensor is a member vibration sensor.

7. The assembly of claim 1, wherein the sensor array is a non-radioactive sensor array.

8. The assembly of claim 1, wherein the assembly is a pipeline monitoring assembly configured to be externally attached to a pipeline.

9. The assembly of claim 8, wherein the pipeline monitoring assembly is a refined oil pipeline monitoring assembly or a crude oil pipeline monitoring assembly.

10. The assembly of claim 1, wherein the density sensor is configured to emit an ultrasonic wave that passes through the flow material in the passage of the member, reflects off of a rear wall portion on the member, and returns to the density sensor.

11. The assembly of claim 10, wherein the controller is configured to determine a density of the flow material based on at least one of a measured speed of the ultrasonic wave and a time that is taken for the ultrasonic wave to pass through the flow material.

12. The assembly of claim 11, wherein determining the density of the flow material includes adjusting the density data sensed by the density sensor based on predetermined properties of the member.

13. The assembly of claim 1, wherein the corrosion sensor is a sensor selected from the group consisting of an eddy-testing-preforming sensor and a peltier-based-measurement sensor.

14. The assembly of claim 1, wherein at least one of air pockets in the flow material, cavitation of the flow material, a presence of debris in the flow material, and a flow direction of the flow material is determined based on the density data sensed by the density sensor and transmitted by the communication device.

15. The assembly of claim 1, wherein a corrosion rate of the member is determined based on the corrosion data sensed by the corrosion sensor and transmitted by the communication device.

16. The assembly of claim 1, wherein a failure of the member is determined based on both a vibration data sensed by the vibration sensor and transmitted by the communication device and a pressure data sensed by the pressure sensor and transmitted by the communication device.

17. The assembly of claim 16, wherein the sensor array further includes a location sensor, and the vibration data and the pressure data are sensed contemporaneously at a same location of the passage sensed by the location sensor.

18. The assembly of claim 1, wherein the sensor array further includes a temperature sensor that is configured to sense a thermal value of the member.

19. The assembly of claim 18, wherein the controller is configured to determine a temperature of the flow material by adjusting the sensed thermal value based on predetermined heat conductivity attributes of the member.

20. An assembly for sensing flow material in a passage of a member, comprising:
   a housing;

a sensor array disposed at least partially in the housing; and an external-surface-mounting attachment portion configured to non-intrusively attach the assembly to a surface;

wherein the sensor array includes a flow material pressure sensor, a flow material density sensor, a flow material corrosion sensor, a member vibration sensor, a temperature sensor, and a location sensor; and wherein the flow material density sensor is a non-radioactive flow material density sensor.

21. The assembly of claim 20, further including a communication device and a controller disposed in the housing.

22. The assembly of claim 21, wherein the controller controls the communication device to transmit sensed data collected by the sensor array at a frequency of between about one transmission per second and about fifty transmissions per second.

23. The assembly of claim 22, wherein the communication device wirelessly transmits the sensed data.

24. The assembly of claim 20, wherein the external-surface-mounting attachment portion includes a non-penetrating attachment device.

25. The assembly of claim 20, wherein the sensor array further includes a sonic boom detector.

26. The assembly of claim 20, further comprising:

a communication device disposed at least partially in the housing; and a controller disposed at least partially in the housing;

wherein a location of unsuitable operation of the passage is determined based on a flow material pressure data sensed by the flow material pressure sensor and transmitted by the communication device and a location data sensed by the location sensor and transmitted by the communication device.

27. The assembly of claim 20, further comprising:

a communication device disposed at least partially in the housing; and a controller disposed at least partially in the housing;

wherein a location of unsuitable operation of the passage is determined based on a member vibration data sensed by the member vibration sensor and transmitted by the communication device and a location data sensed by the location sensor and transmitted by the communication device.

28. An assembly for sensing flow material in a passage of a member, comprising:

a housing;

a communication device disposed at least partially in the housing;

a controller disposed at least partially in the housing;

a sensor array disposed at least partially in the housing; and an external-surface-mounting attachment portion configured to non-intrusively attach the assembly to a surface;

wherein the sensor array includes a pressure sensor, a density sensor, a corrosion sensor, a vibration sensor, a temperature sensor, and a location sensor;

wherein the controller controls the communication device to transmit sensed data collected by the sensor array at a frequency of between about one transmission per second and about fifty transmissions per second;

wherein the sensed data includes at least one of a density data sensed by the density sensor and a corrosion data sensed by the corrosion sensor; and wherein the density sensor is a non-radioactive density sensor.

29. The assembly of claim 28, wherein:

the density sensor is configured to emit an ultrasonic wave that passes through the flow material in the passage of the member, reflects off of a rear wall portion on the member, and returns to the density sensor;

the controller is configured to determine a density of the flow material based on at least one of a measured speed of the ultrasonic wave and a time that is taken for the ultrasonic wave to pass through the flow material; and determining the density of the flow material includes adjusting the density data sensed by the density sensor based on predetermined properties of the member.

* * * * *